(12) United States Patent
Cole et al.

(10) Patent No.: US 6,579,929 B1
(45) Date of Patent: Jun. 17, 2003

(54) STABILIZED SILICA AND METHOD OF MAKING AND USING THE SAME

(75) Inventors: William M. Cole, Clinton, OH (US); Timothy L. Tartamella, Silver Lake, OH (US); Sanjeev D. Naik, Fairlawn, OH (US); William L. Hergenrother, Akron, OH (US); Georg G. A. Bohm, Akron, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 09/487,860

(22) Filed: Jan. 19, 2000

(51) Int. Cl.$^7$ ................................................ C08K 3/34
(52) U.S. Cl. .................................. 524/492; 524/493
(58) Field of Search ............................. 524/492, 493

(56) References Cited

U.S. PATENT DOCUMENTS

| | | | |
|---|---|---|---|
| 2,736,668 A | 2/1956 | Broge | 106/308 |
| 2,739,078 A | 3/1956 | Broge | 106/308 |
| 2,801,185 A | 7/1957 | Iler | 106/288 |
| 2,993,809 A | 7/1961 | Bueche et al. | 117/100 |
| 3,360,498 A | 12/1967 | Rawlings | 260/45.7 |
| 3,691,129 A | 9/1972 | Burke, Jr. | 260/33.6 AO |
| 3,904,787 A | 9/1975 | Trebinger et al. | 427/220 |
| 4,015,031 A | 3/1977 | Reinhardt et al. | 427/213 |
| 4,072,796 A | 2/1978 | Reinhardt et al. | 428/405 |
| 4,076,550 A | 2/1978 | Thurn et al. | 106/288 |
| 4,208,316 A | 6/1980 | Nauroth et al. | 260/37 SB |
| 4,273,589 A | 6/1981 | Nauroth et al. | 106/308 Q |
| 4,308,074 A | 12/1981 | Nauroth et al. | 106/309 |
| 4,474,908 A | 10/1984 | Wagner | 523/213 |
| 4,643,946 A | 2/1987 | Brauer et al. | 428/372 |
| 5,009,874 A | 4/1991 | Parmentier et al. | 423/335 |
| 5,200,477 A | 4/1993 | Baker et al. | 526/74 |
| 5,376,172 A | 12/1994 | Tripp et al. | 106/490 |
| 5,651,921 A | 7/1997 | Kaijou | 252/309 |
| 5,708,503 A | 1/1998 | Jalics et al. | 523/200 |
| 5,714,533 A | 2/1998 | Hatakeyama et al. | 524/140 |
| 5,763,388 A | 6/1998 | Lightsey et al. | 523/212 |
| 5,780,531 A | 7/1998 | Scholl | 523/213 |
| 5,798,009 A | 8/1998 | Teratani | 152/548 |
| 5,854,327 A | 12/1998 | Davis et al. | 524/445 |
| 5,866,171 A | 2/1999 | Kata | 425/46 |
| 5,866,650 A | 2/1999 | Lawson et al. | 524/572 |
| 5,872,176 A | 2/1999 | Hergenrother et al. | 524/494 |
| 5,876,527 A | 3/1999 | Tsurata et al. | 152/541 |
| 5,902,226 A | 5/1999 | Tasaki et al. | 516/34 |
| 5,908,660 A | 6/1999 | Griffith et al. | 427/220 |
| 5,931,211 A | 8/1999 | Tamura | 152/209.5 |
| 5,939,484 A | 8/1999 | Araki et al. | 524/492 |
| 5,942,590 A | 8/1999 | Burns et al. | 528/10 |
| 5,948,700 A | 9/1999 | Zheng et al. | 438/694 |
| 5,948,842 A | 9/1999 | Araki et al. | 524/261 |
| 5,958,380 A | 9/1999 | Winston et al. | 424/48 |
| 5,958,640 A | 9/1999 | Hasegawa et al. | 430/109 |
| 5,965,110 A | 10/1999 | Arnold | 424/44 |
| 5,968,470 A | 10/1999 | Persello | 423/339 |
| 5,971,046 A | 10/1999 | Koch et al. | 152/152.1 |
| 5,972,087 A | 10/1999 | Uraki et al. | 106/31.65 |
| 5,985,953 A | 11/1999 | Lightsey et al. | 523/212 |
| 5,989,378 A | 11/1999 | Liu et al. | 156/241 |
| 5,997,620 A | 12/1999 | Kodama et al. | 106/3 |
| 5,998,073 A | 12/1999 | Kuramoto et al. | 430/106 |
| 6,004,539 A | 12/1999 | Longo, Jr. et al. | 424/49 |
| 6,004,715 A | 12/1999 | Suzuki et al. | 430/111 |
| 6,008,295 A | 12/1999 | Takeichi et al. | 525/105 |
| 6,012,969 A | 1/2000 | Ryoke et al. | 451/41 |
| 6,025,455 A | 2/2000 | Yoshitake et al. | 528/10 |
| 6,051,672 A | 4/2000 | Burnes et al. | 528/10 |

FOREIGN PATENT DOCUMENTS

| | | | |
|---|---|---|---|
| DE | 195 40 623 A1 | 5/1997 | |
| DE | 199 33 819 A | 2/2001 | |
| EP | 0881 192 A1 | 5/1998 | .......... C01B/33/145 |
| EP | 0890 600 A1 | 6/1998 | .............. C08J/3/21 |
| EP | 0940 428 A1 | 2/1999 | ............ C08K/3/00 |
| EP | 0 982 268 A | 3/2000 | |
| WO | WO 98/53004 | 5/1998 | ............ C08K/9/06 |
| WO | WO 99/15583 | 8/1998 | ............ C08K/9/06 |
| WO | WO 01/52618 A3 | 7/2000 | |

OTHER PUBLICATIONS

Hi–Sil 190G Reinforcing Silica, PPG, 1995.
PPG Silicas Dust Exposure and OSHA Regulations, PPG, 1993.
Hi–Sil Products 200 Series Silicas, PPG, 1991.
Krysztafkiewicz et al.: "Effect of surface modification on physicochemical properties of precipitated silica." Journal of Materials Science, Mar. 1, 1997, vol. 32, No. 5, p. 1334.

Primary Examiner—Edward J. Cain
(74) Attorney, Agent, or Firm—Meredith E. Palmer; Rodney Skoglund

(57) ABSTRACT

A surface stabilized, non-agglomerated silica is provided. The silica is prepared by the method of providing non-agglomerated silica, and then treating the surface of the silica, thereby substantially preventing agglomeration of silica. The surface of the silica may be treated with a hydrophobating agent, such as a silane, or an alcohol. Different embodiments of the invention illustrate that the hydrophobating agent or alcohol can be added at different points within the process of forming the surface stabilized, non-agglomerated silica. The surface stabilized, non-agglomerated silica has a size in the nanometer range. The surface stabilized, non-agglomerated silica can be used as an additive in any application that uses silica, such as reinforcing fillers for elastomeric compositions, foods, drugs, dentifrices, inks, toners, coatings and abrasives.

17 Claims, 7 Drawing Sheets

STABILIZED SILICA AND METHOD OF MAKING AND USING THE SAME

TECHNICAL FIELD OF THE INVENTION

The present invention relates to surface modified silica, methods of making and using the same.

BACKGROUND OF THE INVENTION

The use of silica as a reinforcing filler has been gaining wide acceptance in a variety of fields. There has also been many attempts in the prior art to treat the surface of precipitated silica to improve the properties of the precipitated silica for use as a reinforcing filler.

Griffith et al., U.S. Pat. No. 5,908,660, disclose a method for preparing hydrophobic silica precipitated silica. The method disclosed by the Griffith et al. reference comprises two steps. The first step involves contacting an aqueous suspension of precipitated silica with an organosilicon compound in the presence of a catalytic amount of an acid to effect hydrophobing of the precipitated silica. In the second step the aqueous suspension of the hydrophobic precipitated silica is contacted with a water-immiscible organic solvent to effect the separation of the hydrophobic precipitated silica from the aqueous phase.

It is important to note that the term "particle", as used in this disclosure, differs from the use of the term as used by others, such as Griffith '660, in that particles described herein are those referred to by those familiar with the art as "primary particles". These are individual, generally spherical units, formed at the early stages of the silica synthesis process, which cannot be subdivided by ordinary means. The measurement of the diameters of these particles (as by electron microscopy), together with the determination of their surface area (as by nitrogen adsorption), will reveal a particle density essentially identical to that of pure silica (about 2.21 g/cm$^3$). Further, the term "aggregate", as used herein, refers to an accumulation of these particles that are tightly held together. Aggregates generally cannot be broken down into particles through mechanical means, particularly when aggregates are being mixed with other materials in a mixing operation. The particle-particle interaction forces are generally too great to be broken.

The term "agglomerate" refers to an accumulation of aggregates that are held together. Agglomerates are generally held together by weaker physical forces and can be separated by mechanical means, such as during a mixing operation. Unfortunately, the Griffith et al reference mischaracterizes precipitated silica as aggregate silica. However, it is widely known and accepted to one having ordinary skill in the art that precipitated silica can only exist in the agglomerated form, not in the aggregate form.

Parmentier et al., U.S. Pat. No. 5,009,874, disclose a method for making a hydrophobic, essentially spheroidal precipitated silica, useful as a reinforcing filler in silicone elastomers. In a first step the precipitated silica in aqueous suspension is hydrophobed with an organosilicon compound. In a second step a water immiscible organic solvent is added to effect separation of the hydrophobic precipitated silica from the aqueous phase. The water immiscible organic solvent is added to the process at a volume (L) to weight (kg) ratio of silica of from 1 to 5 and preferably from 1.5 to 4.5.

Nauroth et al., U.S. Pat. No. 4,208,316, U.S. Pat. No. 4,273,589 and U.S. Pat. No. 4,308,074, disclose the treatment of dried precipitated silica with organosilicon compound hydrophobing agents in a ratio of 10:0.5 to 10:3. The product obtained thereby is tempered for 60 to 180 minutes, preferably 70 to 130 minutes, at a temperature of 200° C. to 400° C.

Reinhardt et al., U.S. Pat. No. 4,072,796, disclose a process where an acidic wet suspension of precipitated silica at a temperature of about 50° C. to 90° C. is hydrophobed with a prepolycondensed organohalosilane or a prepolycondensed mixture of organohalosilanes. The hydrophobed precipitated silica is filtered, washed, dried, and tempered at about 300° C. to 400° C.

Reinhardt et al., U.S. Pat. No. 4,015,031, disclose a process where a precipitated silica in powdered form is heated to a temperature of about 200° C. to 300° C. with agitation to fluidize and then treated dropwise with an organosilane which is stable and boils below 300° C.

Treblinger et al., U.S. Pat. No. 3,904,787, disclose the treatment of a precipitated silica in aqueous suspension with an organohalosilane at a temperature within a range of 15° C. to 70° C. The hydrophobic precipitated silica is filtered, washed, dried, and tempered by heating in the range of 200° C. to 500° C.

Although all of the prior art attempts described hereinabove are methods to treat agglomerated precipitated silica, none of the references attempt to stabilize the surface of non-agglomerated silica.

There have been alternative attempts to provide stabilized non-agglomerated silica. Once such attempt is described in European Patent Publication No. 881192, which is a process for producing a hydrophobic organosilica sol comprising a colloidal silica stabilized and dispersed in a hydrophobic organic solvent, which does not contain agglomerate. The stabilized silica of this reference is prepared in a solvent, such as ketones and esters, which are not compatible with rubber synthesis techniques. Therefore, it remains desirable in the art to provide surface-stabilized, non-agglomerated silica that is compatible with rubber compositions and rubber synthesis.

SUMMARY OF THE INVENTION

It would be advantageous to employ stabilized non-agglomerated silica for purposes of reinforcing rubber compositions to avoid the need to divide the large agglomerates of precipitated silica into smaller aggregates. The use of non-agglomerated silica, results in the reduction of energy costs in rubber compounding, and also avoids degradation of the polymer that is traditionally associated with the division of large agglomerates of precipitated silica into smaller silica particles.

The present invention provides a process for preparing surface-stabilized, non-agglomerated silica dispersed within a polymer. The process of the present invention comprises the steps of providing colloidal silica; stabilizing the surface of the colloidal silica; and blending the surface-stabilized silica with a polymer solution and, optionally, at least one additive, thereby substantially preventing agglomeration of silica.

The present invention further provides a surface-stabilized, non-agglomerated silica dispersed in a polymer, wherein the silica size is less than about 50 nanometers.

The present invention also provides a process for preparing a surface-stabilized, non-agglomerated, silica comprising the steps of: providing colloidal silica in a first solvent; stabilizing the surface of the silica, wherein the stabilizing comprises: performing a solvent exchange operation with an alcohol, whereby the first solvent is exchanged for the alcohol; adding alcohols capable of esterifying the silica; and esterifying the silica to provide stabilized, non-agglomerated silica in alcohol.

The present invention also provides a process for preparing a surface-stabilized, non-agglomerated, silica comprising the steps of: providing colloidal silica in a first solvent; stabilizing the surface of the silica, wherein the stabilizing comprises: performing a solvent exchange operation with a non-aqueous, non-alcohol solvent, whereby the first solvent is exchanged for the non-aqueous, non-alcohol solvent; adding at least one hydrophobating agent to produce provide stabilized, non-agglomerated silica in a non-aqueous, non-alcohol solvent.

The present invention also provides for pneumatic tires, orally inserted compounds, polishing compositions, and inks and toners that use surface-stabilized, non-agglomerated silica of the present invention.

A feature of the invention is the stabilization of silica particles and/or aggregates before they have a chance to agglomerate.

An advantage of the invention is the avoidance of several commercial processing steps to create precipitated silica and then break it down into a size suitable for elastomeric polymer processing.

Another advantage of the invention is cost savings associated with reduction in processing steps. Another advantage of the invention is less variance in size for elastomeric polymer processing, such as physical mixing.

As used throughout this Specification, the following definitions apply:

The term "slurry" refers to a thin paste produced by mixing an insoluble substance with enough solvent to allow the mixture to flow viscously.

The term "organosol" refers to the colloidal dispersion of an insoluble material in an organic liquid.

The term "alcosol" refers to the colloidal dispersion of an insoluble material in an alcohol.

The term "stabilized" refers to being substantially unable to form an aggregate or an agglomerate via normal physical means.

The phrase "solvent exchange" refers to the process where one solvent replaces another solvent in a solution, slurry, or sol.

The phrase "surface stabilized, non-agglomerated silica" refers to silica that has been surface treated without agglomeration of the silica.

The term "masterbatch" refers to any blend of silica with other additives, such as a blend of modified silica with a polymer; a blend of modified silica, polymer and an oil; and a blend of modified silica, polymer, oil, and other additives.

DETAILED DESCRIPTION OF THE INVENTION

Figure 1:
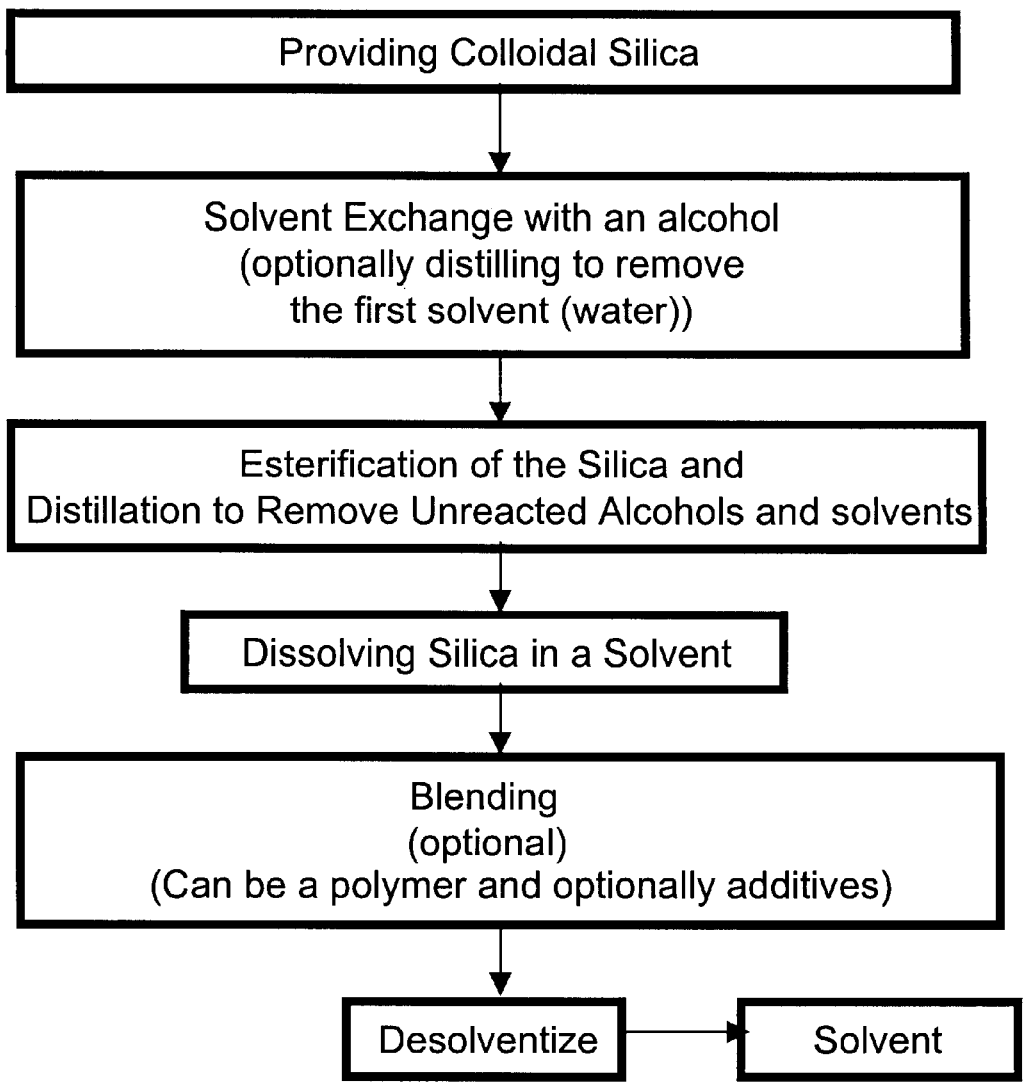
FIG. 1 is a flow chart representing one embodiment of the present invention, in which the surface stabilized, non-agglomerated silica is stabilized by esterification.
Figure 2:
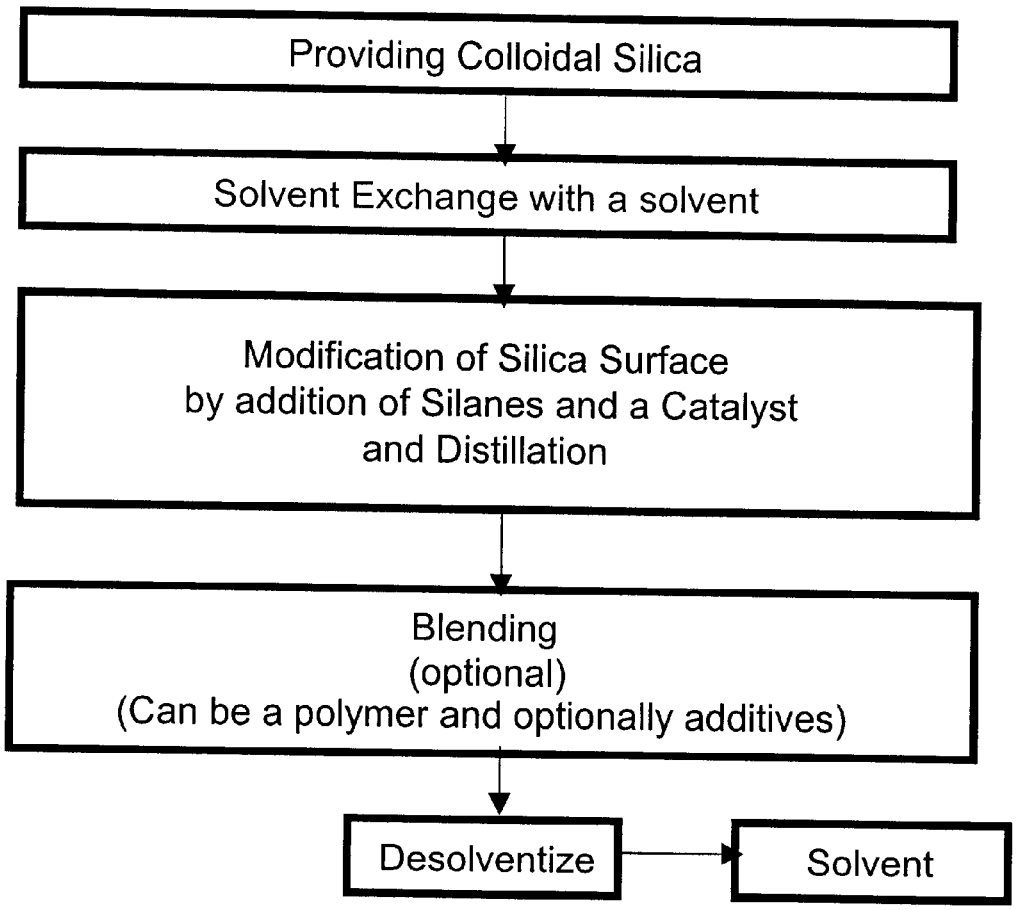
FIG. 2 is a flow chart representing one embodiment of the present invention, in which the surface stabilized, non-agglomerated silica is surface stabilized with hydrophobating agents, such as silanes.
Figure 3:
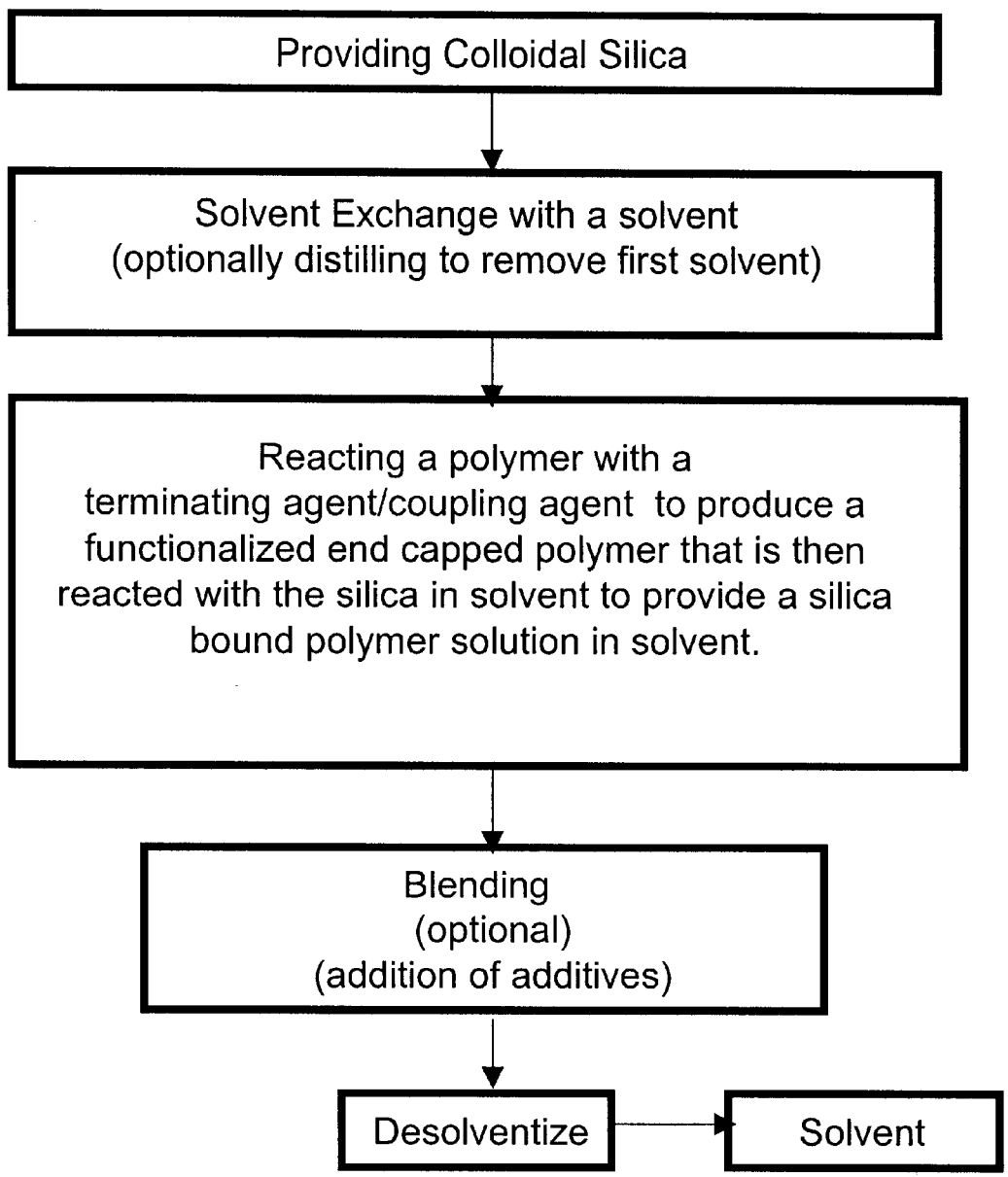
FIG. 3 is a flow chart representing one embodiment of the present invention, in which the surface stabilized, non-agglomerated silica prepared by the process outlined in FIG. 2 is reacted with a functionalized polymer to provide a silica bound polymer solution.
Figure 4:
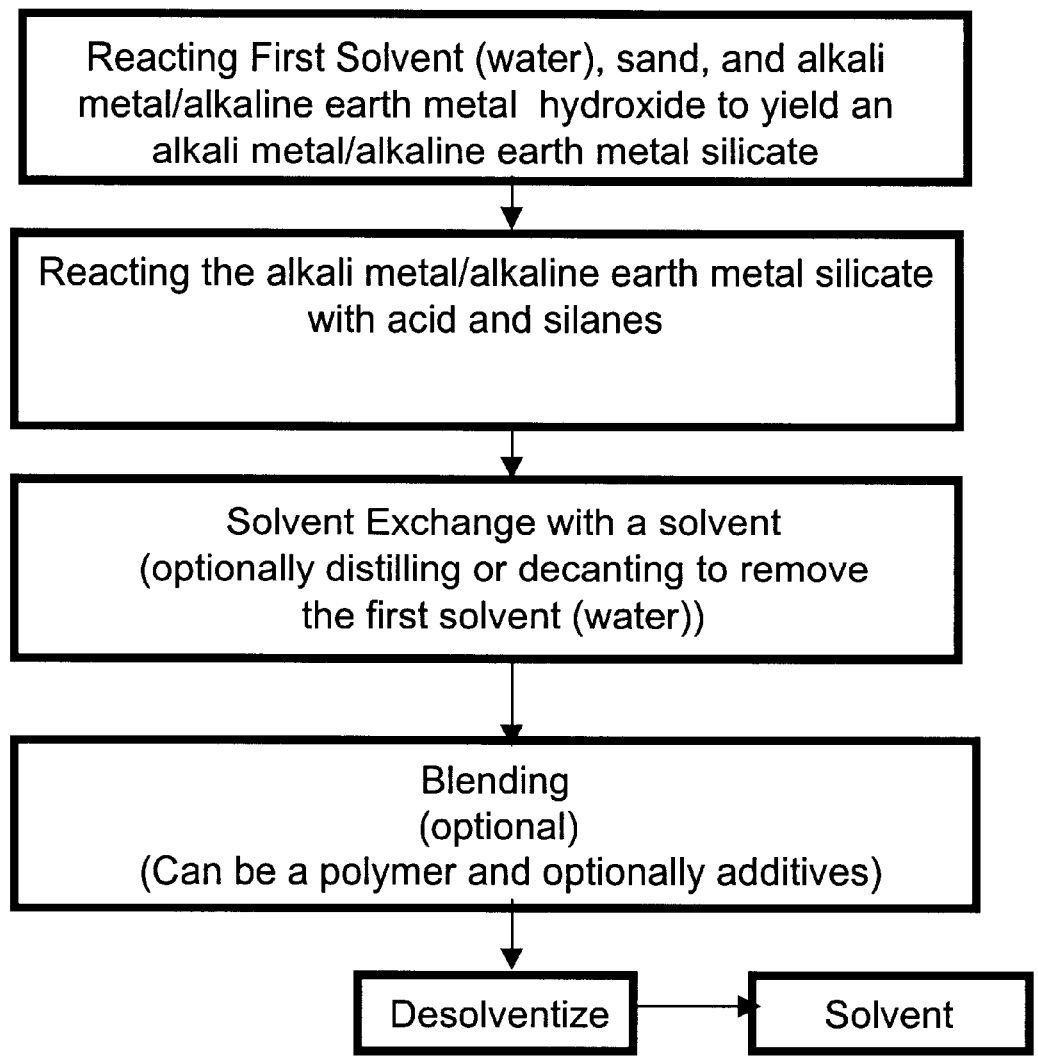
FIG. 4 is a flow chart representing one embodiment of the present invention, in which the surface stabilized, non-agglomerated silica is prepared by the route where silanes are added at the formation step of the colloidal silica.
Figure 5:
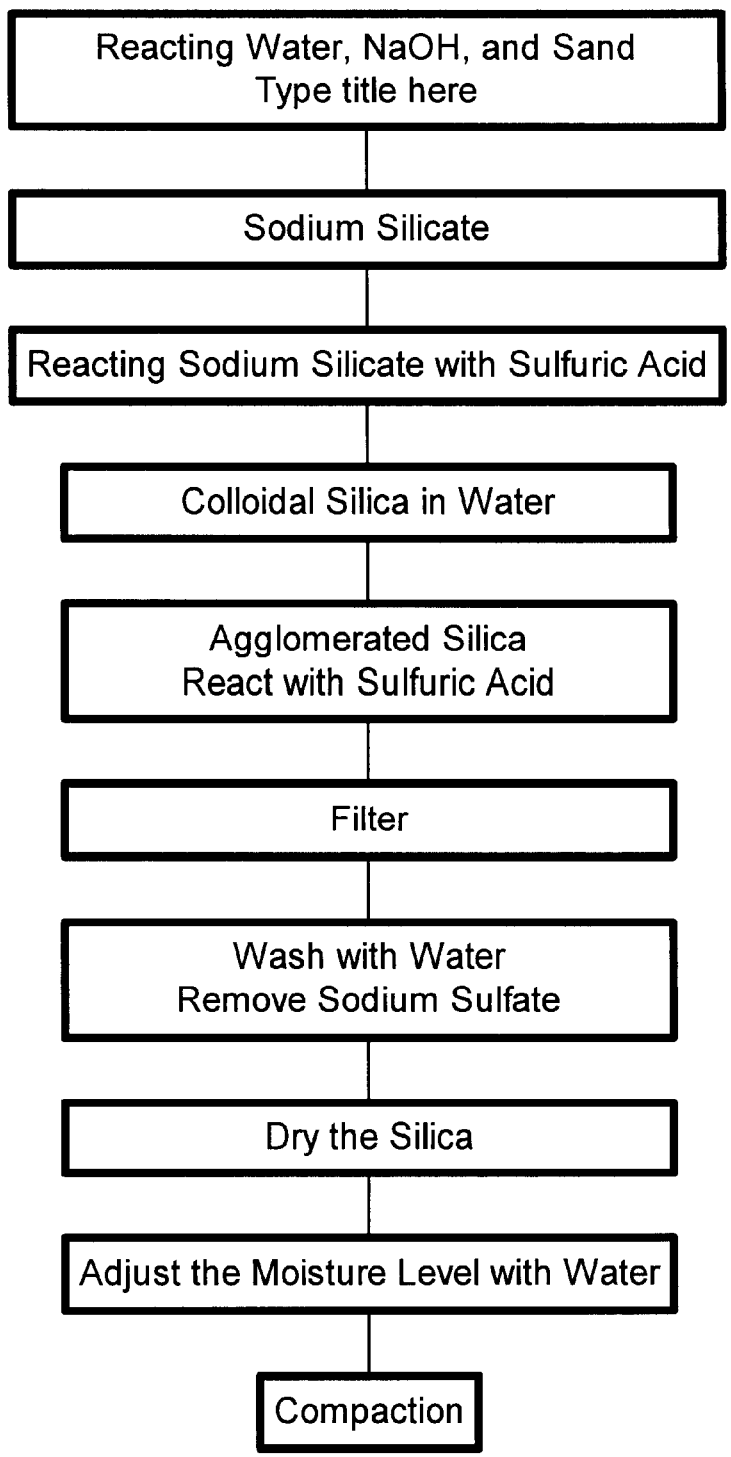
FIG. 5 is a flow chart representing one prior art process for the production of agglomerated silica.

In the conventional preparation of precipitated silica, the colloidal silica strongly associates into aggregates, which in turn combine less strongly into agglomerates. By the practice of this invention, the surface of the non-agglomerated silica is stabilized thereby substantially preventing subsequent agglomeration of the silica. In contrast to the conventional preparation of precipitated silica, the present invention provides a process for preparing surface-stabilized, non-agglomerated silica dispersed in a polymer. The process of the present invention comprises providing colloidal silica having stable silica particle sizes, which substantially prevents the subsequent agglomeration of silica.

In one embodiment, colloidal silica in a first, preferably aqueous, solvent is provided. In a first step, a solvent exchange operation is performed with an alcohol, whereby the first solvent is exchanged for the alcohol. The non-agglomerated silica in the alcohol is then esterified. The unreacted alcohols and any water that may be present may be removed by any suitable means, such as by distillation.

Optionally, the esterified silica particles are dissolved in an organic solvent to form an organosol. The organosol can optionally then be blended with a polymer solution and, optionally, at least one additive to form a masterbatch. The masterbatch is desolventized thereby forming surface-stabilized, non-agglomerated silica dispersed within a polymer. The organic solvents are preferably at least one of a $C_4$–$C_{20}$ aliphatic, $C_5$–$C_{20}$ cycloaliphatic, $C_6$–$C_{20}$ aromatic, and $C_6$–$C_{20}$ alkyl aromatic.

Additionally, the solvent exchange operation can include a distillation step to remove the first solvent.

Generally, the first solvent is water because a typical method of providing silica is in the form of aqueous colloidal silica. Colloidal silica is typically prepared by reacting sand with an alkali metal/alkaline earth metal hydroxide in water (the first solvent). Preferably, the hydroxide is sodium hydroxide. The reaction product forms an alkali metal/alkaline earth metal silicate. This reaction product is then further reacted with an acid, to form the colloidal silica. Preferably, the concentration of the silica in the first solvent ranges from about 1% to about 70% by weight, and even more preferably from about 10% to about 50%. If the colloidal silica is prepared in an alcohol, the solvent exchange operation is not required. Acids that can be used in the reaction include, but are not limited to, hydrohalides, sulfuric acid, phosphoric acid, carboxylic acids, carbon dioxide, acidic ion exchange resins, and mixtures thereof. Preferably, the acid is sulfuric acid.

Useful colloidal silicas include Ludox™ AM-300 colloidal silica (E.I. DuPont de Nemours; Wilmington, Del.), MEK-ST™ colloidal silica in methylethyl ketone (Nissan Chemical Industries, Ltd.;Tokyo, Japan), or colloidal silica synthesized as described above.

Suitable alcohols for the solvent exchange operation include, but are not limited to, monohydric, low molecular weight alcohols. Preferably, the alcohol is a $C_1$ to $C_6$ linear or branched alkyl alcohol. The preferred alcohol for the solvent exchange operation is isopropanol.

The silica in alcohol concentration ranges from about 1% to about 70% by weight. Preferably, the silica in alcohol concentration ranges from about 10% to about 50% by weight.

Generally, the esterification process can be illustrated as follows. Solvent exchange with a first alcohol, preferably water miscible, is carried out, preferably by distillation, resulting in an alcosol with untreated colloidal silica particles as the dispersed phase in a water-miscible alcohol as a continuous phase. The choice of the first alcohol can be, but is not restricted to, alcohols like methanol, ethanol, isopropanol, n-propanol, t-butyl alcohol, and other water miscible alcohols like 2-methoxy ethanol, 2-ethoxy ethanol, etc. In a preferred embodiment, isopropanol is used as the first alcohol of choice for the preparation of the alcosol.

A monohydric, preferably water-immiscible, alcohol is then added as the esterification reagent and heated. The esterifying agent can be a monohydric alcohol, such as a linear or branched, unsaturated or saturated, alkyl or aryl alkyl alcohol preferably containing at least four carbon atoms. Preferably, the alcohols are monohydric $C_4-C_{20}$ alcohols. Among the preferred aliphatic alcohols are n-butyl, n-hexyl, n-heptyl, n-octyl, n-nonyl, n-decyl, n-undecyl, n-dodecyl, n-tetradecyl, n-hexadecyl, n-octadecyl, etc. Also preferred, the esterifying alcohol may be a mixture of octanol and hexanol. If the reaction is to be carried out at atmospheric pressure, a high boiling alcohol such as n-hexanol or n-octanol is preferred, so as to be able to conduct the esterification reaction at higher temperatures (about 160° C. to about 200° C.) at reflux. Alternatively, lower molecular weight alcohols can be used, but the esterification is performed at pressures greater than atmospheric pressure.

The first alcohol is removed and replaced eventually by the esterification alcohol. In a preferred embodiment, a lower boiling alcohol like hexanol is first added, replacing isopropanol. To further increase the temperature for effective esterification, a higher boiling alcohol like octanol is preferred. Thus, once all the isopropanol is driven away, octanol can be added, further raising the temperature. Direct addition of the octanol, without the hexanol-addition step, is also possible. However, precipitation of the silica out of solution is possible if a high boiling water-immiscible alcohol is added directly to the isopropanol based alcosol. Preferably, slow addition of hexanol followed later by octanol is used to obtain stable sols. Some esterification by hexanol is possible during the step of removal of the original water-miscible alcohol.

Large excesses of alcohol are preferred in this embodiment, driving the equilibrium esterification reaction towards the right. Surface-esterification is carried out for about 3 to about 10 hours.

However, the use of catalysts can increase the rate of the reaction and reduce the amount of alcohol required. Typical catalysts include, but are not limited to, the following general classes of catalysts. Amine compounds of formula $NR^7_3$ or $NR^7 R^8 R^9$ used to promote the reaction(s) are selected from the group where $R^7$, $R^8$, and $R^9$ may be the same or different, H, alkyl, aryl, cycloalkyl, alkenyl, alkynyl, and their derivatives, containing, but not limited to F, Cl, Br, I, O, and N. Substituents $R^7$, and $R^8$ may also be part of an aliphatic or aromatic ring. Examples of suitable bases that may be employed are non-, mono-, di- and tri-substituted alkyl and aryl amines and include, but are not limited to, $NH_3$, methyl amine, dimethylamine, trimethylamine, methylethylamine, methylethylisobutyamine, dodecylamine, triethylamine, perfluorotriethylamine, perchlorotrimethylamine, pyridine, ethanolamine, 1,4-dimethylaminobutane, and the like, and mixtures thereof. Condensation catalysts like dibutyl amines, di-n-hexylamine, triethanolamine, triethyl amine, diethyl amine, dicyclohexylamine, di-n-octylamine, and trimethylbenzyl amine can be used. Additionally, condensation catalysts such as organometalic compounds, silazanes, and the like, can also be used. The organometalic compounds are preferably organic acid salts of lead, tin, zinc, cobalt, and titanium. Organic acids are preferably octyl acid, acetic acid, lauric acid, and maleic acid. The following are non-limiting examples of organometalic compounds: dibutyltindiacetate, dibutyltindilaurate, dioctyltindilaurate, tin octanoate, tin octoate, stannous oleate, stannous, tetraisopropyltitanate, and diisopropylbis (acetoacetic/acid ethyl) titanium.

Preferably, water that is liberated during esterification is removed. The water can be removed by molecular seives used in a Dean-Stark trap being used along with a condenser. Surface-esterified silica present in alcohol is thus obtained. The alcohol is driven away by any suitable means, such as vacuum distillation, leaving the esterified silica as a viscous grease. The esterified silica can be then easily dispersed in the organic solvent of choice, hexane in our case. The degree of esterification can be characterized by a carbon content analysis of the silica.

The degree of esterification of the silica particles in the organosol can be determined from a dry powder used in measuring the nitrogen surface area. The organosol is dried in a vacuum at 110° C. until all of the organic solvent is removed. The surface of the resulting powder is then determined by nitrogen adsorption. The carbon content of the powder is determined by igniting the sample, collecting and weighing the resulting carbon dioxide. From the carbon content and the surface area in square meters per gram the degree of esterification can be calculated according to the equation: $D.E.=(500\%C)/nA_n$ wherein D.E. in the degree of esterification in ester groups per square nanometer, % C is the percent carbon, n is the number of carbon atoms in the alcohol of the organosol and $A_n$ is the surface area, in square meters per gram, of the silica powder derived from the organosol.

The desolventization step can be performed by any known desolventization process. One method of performing desolventization is the addition of steam and water to remove the solvent. If using the steam and water desolventization method, a drying step is used to remove the residual water by the application of heat and/or vacuum. Additionally, desolventization can be accomplished by internal mixers or by two roll mills.

In another embodiment, colloidal silica in a first, preferably aqueous, solvent is provided. A solvent exchange operation is performed with a second (preferably non-aqueous, non-alcohol) solvent, whereby the first solvent is exchanged for the second solvent. The colloidal silica suspended in the second solvent is reacted with an effective amount of a hydrophobating agent, preferably a silane, to produce a slurry or organosol.

Optionally, the slurry or organisol is then blended with a polymer solution and, optionally, at least one additive to form a masterbatch. The masterbatch is desolventized to form surface-stabilized, non-agglomerated silica dispersed within a polymer.

Generally, the surface stabilized route can be illustrated as follows. The process is illustrated using the preferred embodiment where the colloid is in water. Starting with colloid of silica, preferably aqueous, an organic solvent is added to form a liquid-liquid dispersion. Solvent exchange by distillation is carried out to azeotropically dehydrate the dispersion. Once all water is removed, a slurry of the silica in the organic solvent of choice is formed.

With the mixture still warm and continued agitation to prevent the silica particles from settling down, the chosen hydrophobating agent(s), preferably a silane or mixture of silanes, is added. If a catalyst is to be used, it can be added prior to or with the hydrophobating agent(s). Sequential addition can benefit from stirring for an effective period of time, preferably about 10–30 minutes. Heating is continued at reflux temperatures (temperature thus depends on the chosen organic solvent) for about 1–10 hours, preferably 3–7 hours. Higher temperatures which may be desirable to drive the reaction faster can be achieved by either using an organic solvent with a higher boiling point, or by operating under higher pressures and consequently higher reflux temperatures.

The amount of hydrophobating agent(s) necessary depends on the amount of hydrophobization desired. Preferably, it is desirable to react or at least shield all the surface silanol groups. Depending on the surface area of the silica particles and an estimate of the number of silanol groups per $nm^2$ surface area, the molar equivalent of the amount of hydrophobating agent(s) required can be estimated. However, with certain hydrophobating agent(s), due to the shielding effect of the long-chain alkyl groups of the hydrophobating agent(s), it is possible that, though a given hydrophobating agent(s) molecule reacts with one silanol group, it can in effect shield multiple silanol groups.

Once the reaction is over, the result is an organosol or a slurry of hydrophobic silica particles directly in the organic solvent of choice. Solvent exchange with another solvent is possible after this step to obtain an organosol in any other solvent of choice.

Again, the solvent exchange step is typically performed when the first solvent is water. If the silica is already provided in the second solvent, the solvent exchange step is not required. Additionally, the solvent exchange step can include distillation to remove the first solvent.

Solvents that can be used as the second solvent in the present invention include, but are not limited to $C_4$–$C_{20}$ aliphatic, $C_5$–$C_{20}$ cycloaliphatic, $C_6$–$C_{20}$ aromatic, and $C_6$–$C_{20}$ alkyl aromatic solvents. Preferably, the second solvent is at least one isomer of hexane, meaning the solvent contains 6 carbon atoms. The silica is present in the second solvent in an amount from about 1% to about 70% based on the weight of the silica.

As described above, the surface of the non-agglomerated silica is stabilized with an effective amount of a hydrophobating agent. Hydrophobating agents that are useful according to the present invention include, but are not limited to those having the general formula $(R_1)_a ZX_b$, wherein each $R_1$ independently comprises $C_1$ to about $C_{20}$ alkyl or alkenyl aliphatic, about $C_5$ to about $C_{20}$ cyclo-aliphatic, or about $C_6$ to about $C_{20}$ aromatic, preferably $C_1$ to about $C_{10}$ aliphatic, about $C_6$ to about $C_{10}$ cyclo-aliphatic, about $C_6$ to about $C_{12}$ aromatic, or $Y(CH_2)_c$ wherein c equals to 1 to 8 and wherein Y is a moiety selected from the group consisting of halo, glycidoxy, mercapto, methacryloxy, and amino moieties; X is Cl, $OR_2$, $OSi(R_2)_3$, or $NHSi(R_2)_2$; each $R_2$ independently contains from one to about 6 carbon atoms; Z is Si or Sn; a is an integer from 1 to 3; and the sum of a and b is 4.

Representative examples of useful silane hydrophobating agents include, but are not limited to, octyltriethoxy silane, octyltrimethyloxy silane, (3-glycidoxypropyl)trimethoxy silane, (3-glycidoxypropyl)triethoxy silane, hexyltrimethoxy silane, ethyltrimethoxy silane, propyltriethoxy silane, phenyltrimethoxy silane, 3-mercaptopropyltriethoxy silane, cyclohexyltrimethoxy silane, cyclohexyltriethoxy silane, dimethyldimethyoxy silane, 3-chloropropyltriethoxy silane, 3-methacryoxypropyltrimethoxy silane, i-butyltriethoxy silane, trimethylethoxy silane, phenyldimethylethoxy silane, hexamethyldisiloxane, trimethylsilyl chloride, dibutyldiethoxy stannane, vinyltriethoxy silane, hexamethyldisilizane, and the like.

The hydrophobating agents are added at a level sufficient to prevent agglomeration. Generally, the amount of hydrophobating agent added ranges from about 0.1% to about 200% based on the weight of the silica. Preferably, the amount of hydrophobating agent is present in an amount from about 1% to about 50% based on the weight of the silica.

To aid in the reaction of the hydrophobating agents with the silica, a catalyst may be used. Typical catalysts include the general classes of catalysts listed above but also can include aminosilanes such as aminopropyl-trimethoxy silane, methyldimethoxy-di-n-hexyl aminosilane) or silazanes such as hexamethyl disilazane, such that the aminosilane provides both the catalyst moiety (amino) as well as the hydrophobating agent moiety.

The catalyst works through interaction with the surface of the silica and hence the amount to be added can be best characterized in terms of the available surface area of the silica surface. Generally, the catalyst is added in an amount enough to cover the silica surface with a submonolayer to an excess of about up to about 10 fold. The catalyst is preferably added in an amount from about 0.01% to about 50%, based on the weight of hydrophobating agent. More preferably, the catalyst is added in an amount from about 0.01% to about 30% based on the weight of the hydrophobating agent.

Optionally, the process can include a step to distill any water, alcohol, or acid that is present to remove such liquids.

In another embodiment, colloidal silica is provided in a first, preferably aqueous, solvent. The colloidal silica then undergoes a solvent exchange operation, whereby the first solvent is exchanged for a second solvent. The silica is then blended with a polymer solution wherein the polymer has functional groups capable of reacting with silica. The blending generates a reaction to provide a silica bound polymer. As above, this reaction can be catalyzed using a catalyst of the type listed above. The silica bound polymer is then desolventized. Optionally, some surface stabilized, non-agglomerated silica that did not react with the polymer may be dispersed within the silica bound polymer.

More specifically, the first step involves the same solvent exchange step described above, in which the water present in the original silica colloidal sol is replaced by a hexane isomer, by azeotropic distillation. If desired, a hydrophobating agent can be added at this point, in a quantity sufficient to prevent the formation of tightly bound silica agglomerates. This slurry of loosely associated silica in hexane is then combined with a freshly polymerized polymer, also in hexane. This freshly polymerized polymer can be any of several candidates, all of which necessarily feature the presence of functional groups which are capable of reacting with silica silanols, wherein these functional groups are hereinafter referred to as "functional terminating/coupling agents". In order to shield any silanols which remain, additional hydrophobating agent(s) may be added to the solution at this point. Additional additives may be added at this point if desired. Solvent is then removed, to produce the final masterbatch material. In this embodiment, a portion of the polymer is chemically bonded to at least a portion of the silica. The relative quantities of unbound silica and polymer will depend on the degree of functionality of the polymer, the quantity of hydrophobating agent added to the silica prior to mixture with the functional polymer, and the ratio of the polymer to the silica in the mixture.

Preferred functional terminating/coupling agents can include, but are not limited to, tetraethoxysilane (TEOS), silicon tetrachloride, or coupled tin tetrachloride.

Again, the solvent exchange step is typically performed when the first solvent is water. If the silica is already provided in the second solvent, the solvent exchange step is not required. Additionally, the solvent exchange step can include distillation to remove the first solvent.

Additionally, the process may further comprise blending at least one additive with the silica bound polymer to form the masterbatch.

The second solvent that can be used in this embodiment is the same as that described in the previous embodiment. Preferably, the second solvent is at least one isomer of hexane.

In another embodiment, the process comprises reacting a silicate of at least one of an alkali metal and an alkaline earth metal in a first, preferably aqueous, solvent, an acid and at least one hydrophobating agent to form a reaction product. The reaction product can be desolventized or distilled to yield a surface stabilized, non-agglomerated silica.

Optionally, before desolventizing, a solvent exchange operation is performed with a second solvent, whereby the first solvent is exchanged for the second solvent. The reaction product in the second solvent is then blended with a polymer solution and, optionally, at least one additive to form a masterbatch. The masterbatch is desolventized to form surface-stabilized, non-agglomerated silica dispersed in a polymer.

The amount of hydrophobating agent reacted with the silicate is an amount sufficient to provide for stabilization of the resultant colloidal silica. Generally, the amount of hydrophobating agent ranges from about 0.01% to about 30% based on the weight of the silicate. Preferably, the amount ranges from about 1% to about 30% based on the weight of the silicate.

The acid can be any acid that will react with the silicate to form a colloidal silica. Examples of the acid include, but are not limited to, hydrohalides, sulfuric acid, phosphoric acid, carboxylic acids, carbon dioxide, acidic ion exchange resins, and mixtures thereof. The preferred acid is sulfuric acid.

Again, the solvent exchange step is typically performed when the first solvent is water. If the silica is already provided in the second solvent, the solvent exchange step is not required. Additionally, the solvent exchange step can include distillation or decantation to remove the first solvent.

The surface stabilized, non-agglomerated silica produced by the process of the present invention is useful in any application that uses silica, such as reinforcing fillers for elastomeric compositions, foods, drugs, dentifrices, inks, toners, coatings and abrasives. The surface stabilized, non-agglomerated silica are particularly useful as reinforcing agents in elastomeric polymer compositions.

The surface-stabilized, non-agglomerated silica product of the present invention has particular application as a reinforcing filler in rubber compositions. The silica bound polymer or silica dispersed polymer can be used as 100 parts of the rubber in a treadstock composition, or alternatively, they can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), including emulsion SBR's, polybutadiene, butyl rubber, neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the silica bound polymers or silica dispersed polymers are blended with conventional rubbers, the amounts can vary widely within a range comprising from about 1 to about 100 percent by weight of the total rubber, with the conventional rubber or rubbers making up the balance of the total rubber (100 parts). It is to be appreciated that the amount of silica bound polymers or silica dispersed polymers will depend primarily upon the degree of reduced hysteresis that is desired. Preferably, for a tread compound, the silica bound polymers or silica dispersed polymers comprise about 30 to about 100 parts of the masterbatch based on a total compound formulation having 200 parts. More preferably, the silica bound polymers or silica dispersed polymers comprise about 80 parts per 200 total part formulation.

Although the vulcanizable elastomeric compounds of the present invention contain silica bound polymer or silica dispersed polymer, the compounds can be optionally compounded with all forms of carbon black in amounts ranging from 0 to about 50 (phr), with about 5 to about 40 phr being preferred. When carbon is present, with stabilized, non-agglomerated polymer bound or dispersed silica, the amount of silica can be decreased to as low as about one phr, otherwise it too is present alone in at least 5 phr.

The carbon blacks may include any of the commonly available, commercially-produced carbon blacks but those having a surface area (EMSA) of at least 20 $m^2$/gram and more preferably at least 35 $m^2$/gram up to 200 $m^2$/gram or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in TABLE 1 hereinbelow.

TABLE 1

Carbon Blacks

| ASTM Designation (D-1765-82a) | Surface Area (m²/g) (D-3765) |
|---|---|
| N-110 | 126 |
| N-220 | 111 |
| N-339 | 95 |
| N-330 | 83 |
| N-351 | 74 |
| N-550 | 42 |
| N-660 | 35 |

The carbon blacks utilized in the preparation of the rubber compounds of the invention may be in pelletized form or an unpelletized flocculent mass. Preferably, for more uniform mixing, unpelletized carbon black is preferred.

Additives that can be used in the present invention for elastomeric compositions include, but are not limited to, processing oils, zinc oxide, zinc stearate, stearic oxide, mineral fillers, organosilanes, fatty acid esters of sugars (preferably $C_5$–$C_6$), talcs, micas, waxes, antioxidants, and coupling agents, such as bis[3-(triethoxylsilyl)propyl] tetrasulfide (Si69). For specific examples of additives that are useful for preparing elastomeric compositions, refer to U.S. Pat. Nos. 5,866,650; 5,872,176; and 5,916,961, all of which are incorporated herein by reference. Additives are generally present in an amount from about 0.1 to about 25 parts of the elastomeric composition.

The elastomeric composition can be cured in a conventional manner with known vulcanizing agents at about 0.2 to about 5 phr. For example, sulfur or peroxide based curing systems may be employed. For a general disclosure of suitable vulcanizing agents, refer to Kirk-Othmer, *Encyclopedia of Chemical Technology*, $3^{rd}$ ed., Wiley Interscience, N.Y., 1982, Vol. 20, pp. 365–468, particularly "Vulcanization Agents and Auxiliary Materials" pp. 390–402. Vulcanizing agents can be used alone or in combination. Preferably, the cure package is not added during the optional blending step of the present invention; it is added after the drying step.

One benefit of the present process for forming the surface stabilized, non-agglomerated silica is realized in the production of elastomeric compositions. When silica is added to elastomeric compositions, it is preferred that the silica be of small size to provide the desired strength and toughness to the elastomeric composition. Prior art silica is agglomerated into large size and requires substantial mechanical mixing to break down the silica. Even though the silica can be broken down, the prior art silica cannot achieve the size of the silica of the present invention.

The mixing operation to break down the silica agglomerates typically is performed in a Banbury mixer, which requires substantial amounts of energy and money to operate. By including a blending step in the production of the silica of the present invention, the expensive Banbury mixing operation can be minimized, if not eliminated. The silica of the present invention is of small enough size so that the high energy mixing is not required. The blending step of the present invention can be carried out in any suitable mixer, such as an extruder, internal mixers, or two roll mixers.

The surface stabilized, non-agglomerated silica of the present invention is distinguished from prior art silicas in that the surface of the silica of the present invention is stabilized before the silica can precipitate out of solution. Prior art precipitated silica is silica that is of large enough size that it is no longer held in colloidal suspension and has precipitated out. To be large enough to precipitate, the silica must be in the form of agglomerates. The prior art treats the silica after it has precipitated.

Without being limited to theory, it is theorized that the surface stabilized, non-agglomerated silica may form agglomerates after the surface has been stabilized. However, because the surface is already stabilized, the energy required to break this type of agglomerate is far less than the energy required to break an agglomerate of silica that has not been surface treated.

Surface stabilized, non-agglomerated silica of the present invention will exist in the form of primary particles, or loosely held agglomerates thereof, typically having a size measured on the nanometer scale. Size of the silica, in a rubber matrix, can be measured by a scanning electron microscope and typically ranges from about 1 nm to about 1000 nm, preferably from about 2 nm to about 100 nm. Correspondingly, the BET surface area of the silica of the present invention can range from about 50 m²/g to more than 1000 m²/g. Alternatively size can be determined from surface area measurements. The organosol is dried in a vacuum at 110° C. until all of the organic solvent is removed. The surface area of the resulting powder is then determined by nitrogen adsorption. The particle diameter, in microns, is then calculated from the surface area, using the relationship: $D=3000/A_n$, wherein D is the particle diameter in nanometers, and $A_n$ is the surface area of the product in square meters per gram.

The use of the surface-stabilized, non-agglomerated silica of the present invention avoids the need to divide the large agglomerates of precipitated silica into smaller aggregates for use as a reinforcing filler. With respect to the field of rubber or tire compounding, the use of non-agglomerated silica is particularly advantageous, because the energy costs to break agglomerates of precipitated silica into smaller aggregates, and the degradation of the rubber polymers that is traditionally associated with the high shear mixing required to divide the large agglomerates of precipitated silica into smaller silica particles can be avoided. The use of surface-stabilized, non-agglomerated silica results in a more uniform or homogenous blending in rubber compositions during compounding procedures.

Surface-stabilized, non-agglomerated silica of the present invention can be used in a variety of products in which precipitated silica has been traditionally used, but adds the unexpected advantage of being surface-stabilized at a size prior to agglomeration. As such, the benefits of non-agglomerated silica can be brought to the industries that have traditionally used precipitated silica but have desired smaller size interaction of the silica with the processes or products otherwise involved.

For example, surface-stabilized, non-agglomerated silica can be used as reinforcing fillers for elastomeric compositions, and in foods, drugs, dentifrices, inks, toners, coatings and abrasives among many other products.

In the case of elastomeric compositions, any number of rubber-based products can benefit from the smaller size of silica more completely dispersed in the polymer and the minimization of energy to produce the silica and disperse into the polymer. Such rubber-based products include tires, hoses, power transfer belts, and the like. The production of pneumatic tires for vehicles and other uses can greatly benefit from reduction of energy employed in Banbury mixing that is required to otherwise reduce the size of commercially available precipitated silica. The use of silica as a reinforcing filler in vehicle tires is known to those skilled in the art from the disclosures of U.S. Pat. Nos. 5,798,009; 5,866,650; 5,872,176; 5,939,484; 5,948,842; and 6,008,295, among many others, the disclosures of which patents are incorporated herein by reference. Particularly the use of silica of the present invention as dispersed in tread rubber is a significant value to the production of vehicle tires, as is known to those skilled in the art to balance of wet traction, ice and snow traction, and rolling resistance, a combination of properties highly desired by tire manufacturers. Briefly, as the rubber component, such rubbers are well known to those skilled in the art and include natural rubber (NR), synthetic polyisoprene rubber, styrene/butadiene rubber (SBR), polybutadiene, butyl rubber, neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. As the rubber component in the present invention, any of the above rubbers can be used singly or as a blend of two or more rubbers. Examples of the synthetic rubber include synthetic polyisoprene rubber, polybutadiene rubber (BR), styrene-butadiene rubber (SBR), butyl rubber, and halogenated butyl rubber. A rubber composition can comprise a rubber component; silica in an amount of 10 to 85 parts by weight and preferably 20 to 65 parts by weight per 100 parts by weight of the rubber component. Pneumatic tires can be made according to the constructions identified in the above incorporated patents, as well as disclosed in U.S. Pat. Nos. 5,866,171; 5,876,527; 5,931,211; and 5,971,046, the disclosures of which are incorporated herein by reference.

In the case of inks and toners, the size of silica is quite important for the delivery of such inks or toners through the printheads of the printers, to minimize clogging of the inks or toners in the printhead. The amount of silica employed in such liquids is known to those skilled in the art from the disclosures of U.S. Pat. Nos. 5,989,378; 5,972,087; 5,998,073; 6,004,715; and 5,958,640. These patents disclose some type of colorant in a liquid along with other additives including silica.

In the case of food, drug, and dental products, because silica is acceptable for human ingestion, the use of silica produced according to this invention can be valuable to those seeking a smaller silica particle that is essentially desolventized prior to mixing with other human ingestible compounds. The amount of silica for such orally inserted compounds is known to those skilled in the art from the disclosures of U.S. Pat. Nos. 5,958,380; 5,965,110; and 5,968,470. These patents disclose compounds selected from the group consisting of foods, pharmaceuticals, and dentifrices.

In the case of surface-contacting materials such as polishing compositions, the use of silica produced according to this invention the use of silica produced according to this invention can be valuable to those seeking a smaller silica particle that is essentially desolventized prior to further processing. The amount of silica employed in such carrier liquids of such materials is known to those skilled in the art from the disclosures of U.S. Pat. Nos. 5,997,620; 5,948,700; 6,012,969; and 6,004,539.

EXAMPLES

Preparation of Example 1

1. 643 g of isopropanol (about 800 ml) was heated to its boiling point in a 2-L resin flask equipped with a Dean Stark trap and condenser.

2. 1180.8 g of LUDOX™-TMA were slowly added (from E.I. DuPont de Nemours, Wilmington, Del.) colloidal silica ($\rho=1.23$ g/ml; 34 wt % $SiO_2$) to 740.7 g (950 ml) of isopropanol with vigorous stirring. Silica did NOT agglomerate on addition but formed a translucent solution.

3. An addition of colloidal silica in isopropanol solution was started (from [2]) to the hot isopropanol (from [1]), with slow $N_2$ purge. Heating was continued to reflux, withdrawing condensate. Additional isopropanol (up to 300 ml) was added if silica seemed to be coming out of solution. Once all the water was removed, the result was a sol of silica in isopropanol. 200 ml more isopropanol was added and transfered sol to a jar.

The resulting sol of silica in isopropanol can be used for further reactions (esterification by higher boiling alcohols). The total weight of the final slurry was 700.7 g (610 ml; ($\rho=1.149$ g/ml). The approximate weight percent of silica in the isopropanol sol was estimated to be about 47 wt %.

4. A one liter round bottom flask was charged with 216.8 g (400 ml) isopropanol and 163.1 g (200 ml) n-hexanol, and mixed thoroughly. 120.3 g alcosol mixture from [3] were added with vigorous stirring. This was added slowly to avoid precipitation of the silica. Heated and stirred and $N_2$ purge. With heating, stirring, and $N_2$ purge, all water was removed isopropanol/water azeotrope, by distillation.

5. Removal of isopropanol continued until a temperature of about 150° C. was reached. At this stage, almost all of the water and isopropanol had been driven away. The reactor was cooled. Molecular sieves were added to distillate side of the Dean Starktrap. 122.8 g(150 ml) was added of hexanol and 81.4 g (100 ml) of octanol to the reactor. The mixture was heated and distillate was allowed to pass through sieves. As the volume of the reactor decreased, more hexanol/octanol was added to the mixture. For example, 101.0 g (125 ml) hexanol and 102.5 g (125 ml) octanol were added after about an hour of initial addition of octanol. Thus, an excess of hexanol/octanol was always maintained and water was liberated during esterification was removed by the molecular sieves. The temperature was further increased beyond 170° C. by addition of octanol. Esterification was carried out for over 4–6 hours at a temperature of approximately 180° C. When the reactor was cooled, with removal of distillate, some greasy material was noticed on the walls of the flask. The solid suspension or sol in octanol (and possibly some hexanol) was poured into another round bottom flask and the alcohol was removed under vacuum. The solid remaining was easily dispersed in hexane. It formed a stable sol with only minimal settling of solids over a 3–4 month period.

To test the properties the above surface-treated silica in rubber compounds, a typical test recipe was used. First, a solution masterbatch of the silica with a rubber was created by mixing 100 parts of a solution of a styrene-butadiene polymer with the silica sol, containing 50 parts of silica, and 10 parts of an aromatic oil. This was then desolventized to remove the hexane.

The silica-dispersed polymer was then added to a 65 g Brabender mixer, with additional additives of 2 parts stearic acid and 1 part of Santoflex 13. The Brabender was preheated to 126° C. The polymer+silica+oil mixture was added at an rpm of 50. The rpm was increased to 60. The rpm was further increased as needed to reach 170° C. in approximately 3.5 minutes after which it was discharged.

The masterbatch material was then added to a remill stage in which 5 parts of Si69 (silane) was added. In this stage, a 65 g Brabender mixer was heated to 100–110° C., the masterbatch material was added at 50 rpm. After 30 seconds, the Si69 was added and the rpm increased to 60. At 145° C. or after 3 minutes, the mixer was discharged.

In a final stage, the remill material was charged at 40 rpm, followed by immediate addition of additional additives like ZnO (3 parts), diphenyl guanidine (DPG) (0.5 parts), mercaptobenzothiazole (MBTS) (1 part), t-butylbenzylthiazole sulfenamide(TBBS) (1 part), and sulfur (1.15 parts). The rpm was increased to 60 and the contents discharged at 105° C.

Preparation of Example 2

To a 1000 cc 3-neck flask with Dean Stark trap and condenser, 200 ml of hexane and 78.9 ml of LUDOX™-TMA (DuPont) silica ($\rho$=1.23 g/ml; 34 wt % $SiO_2$) aquasol were added. The mixture was heated to remove the two-phase hexane-water azeotrope. Water azeotroped over was removed from the Dean Stark trap, removing almost 98–99% of the water present in the mixture. Silica was seen as a fluid lower phase, presumably silica with some adsorbed surface water, when stirring was stopped.

With the flask still warm, 4.8 ml of octyltriethoxysilane and 3.6 ml of 3-aminopropyltriethoxysilane were added. The mixture was then heated to reflux; temperature being equal to the boiling point of hexane, which is 68° C. Evolution of ethanol, and possibly some water, was seen. Reflux was continued for about an hour, when no further evolution of ethanol/water was seen. On cooling, material in the flask separated into a clear upper phase and very fine white solid lower phase. Analysis of the liquid phase for silanes indicated that almost all the 3-aminopropyltriethoxysilane and approximately 41% of the octyltriethoxysilane had reacted with the silanol groups on the silica surface.

The silica slurry in hexane obtained above was mixed with 100 parts of a styrene-butadiene rubber, in such proportion that the silica content of the mix was 50 parts, and 10 parts of a mineral oil. After mixing these in a Waring Blender for about a minute, it was steam-water desolventized forming a nice crumb, with no loss of the silica to the water phase. After drying the sample, it was submitted for compounding.

The silica-dispersed polymer was added to a 65 g Brabender mixer preheated to 95–100° C. The Brabender was preheated to 126° C. The desolventized and dried polymer+silica+oil crumbs were added at an rpm of 50. Pigments and additives, 2 parts stearic acid and 1 part of Santoflex 13, were added and the rpm was increased to 60. The rpm was further increased as needed to reach 170° C. in approximately 6 minutes after which it was discharged.

The masterbatch material was then added to a remill stage in which 5 parts of Si69 (silane) was added. In this stage, a 65 g Brabender mixer was heated to 95–100° C., the masterbatch material was added at 50 rpm. After 30 seconds, the Si69 was added and the rpm increased to 60. At 145–150° C., the mixer was discharged. In a final stage, the remill material was charged at 40 rpm, followed by immediate addition of additional additives like ZnO (3 parts), DPG (0.5 parts), MBTS (1 part), TBBS (1 part), and sulfur (1.15 parts). The rpm was increased to 60 and the contents discharged at 110° C.

Preparation of Control for Examples 1 and 2

100 parts of styrene butadiene rubber (SBR) were dry mixed into 50 parts of precipitated silica in a 65 g Brabender mixer along with 10 parts of an aromatic oil, 2 parts of stearic acid, and 1 part of Santoflex 13. The Brabender was preheated to 126° C. The polymer was added at an rpm of 50. The silica, oil, and pigments were then added. The rpm was increased to 60. The rpm was further increased as needed to reach 170° C. in approximately 3.5 minutes after which it was discharged.

The masterbatch material was then added to a remill stage in which 5 parts of Si69 (silane) was added. In this stage, a 65 g Brabender mixer was heated to 100–110° C., the masterbatch material was added at 50 rpm. After 30 seconds, the Si69 was added and the rpm increased to 60. At 145° C. or after 3 minutes, the mixer was discharged. In a final stage, the remill material was charged at 40 rpm, followed by immediate addition of additional additives like ZnO (3 parts), DPG (0.5 parts), MBTS (1 part), TBBS (1 part), and sulfur (1.15 parts). The rpm was increased to 60 and the contents discharged at 105° C.

Results of Example 1 and Control

A comparison of the mechanical properties of the rubber obtained by using a solution masterbatch using the surface esterified silica versus a control test recipe as below is given the Table 2 below.

TABLE 2

| Compound | G' max Mpa | ΔG' MPa | tan δ (@ 7% strain) |
|---|---|---|---|
| Dry Mixed Control | 3.529 | 1.62 | 0.1648 |
| Solution Masterbatch (Alcosol route) | 2.912 | 1.06 | 0.1213 |

Figure 6:
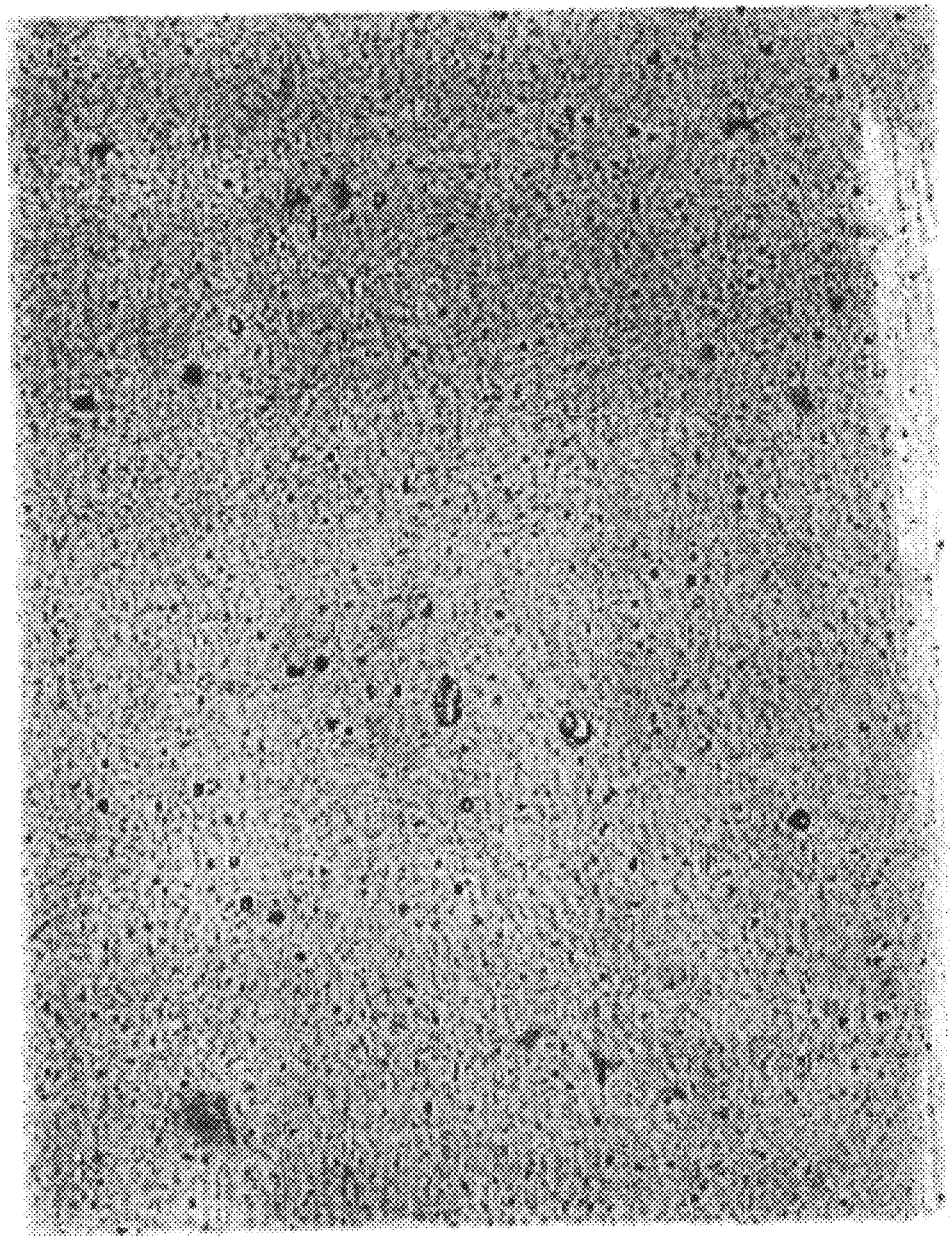
FIG. 6 is a photomicrograph of a silica of the present invention in a polymer composition at 200× magnification.
Figure 7:
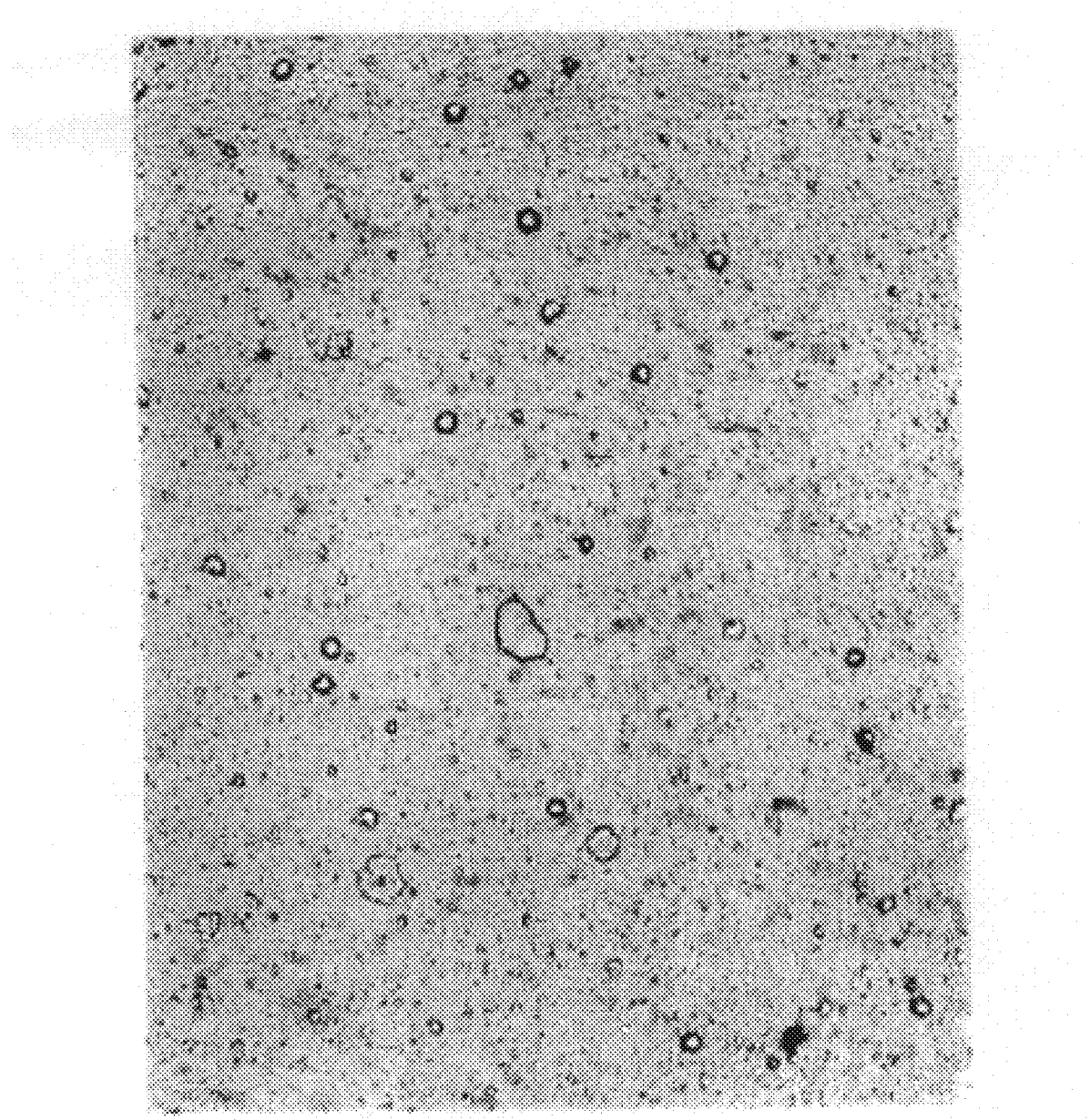
FIG. 7 is a photomicrograph of a prior art silica in the polymer composition of FIG. 6 at 200× magnification.

As can be seen, superior properties are obtained by the silica solution masterbatch route, yielding good hysteresis properties, indicating better dispersion of the silica in the rubber compound. FIGS. 7 and 6 show optical micrographs for the above control and test samples, respectively, showing better dispersion of the silica in the rubber compound for the silica solution masterbatch sample.

The resulting rubber composition was then observed at 200× magnification by an optical microscope. FIG. 6 shows the small size silica in polymer obtained by this method. In comparison, FIG. 7 shows a rubber composition, prepared as in the Comparative Example below, containing a prior art agglomerated silica observed at 200× magnification by an optical microscope. Even though the prior art silica is mixed, the mixing energy is not able to break the agglomerated silica of the prior art down to particles of silica that can be achieved by the methods of the present invention.

Results of Example 2 and Control

A comparison of the mechanical properties of the rubber obtained by using the solution masterbatch using the surface-silylated silica versus a control test recipe as above is given the Table 3 below. Results from muffle furnace oxidation show that the silica loading in both samples was approximately the same. The better hysteresis properties indicate better dispersion of the silica in the rubber compound.

TABLE 3

| Compound | % SiO₂ (muffle furnace oxidation) | G' max MPa | ΔG' MPa | Tan δ (@ 7% strain) |
|---|---|---|---|---|
| Dry Mixed Control | 30.70 | 3.15 | 1.31 | 0.169 |
| Solution Masterbatch (Hydrophobating agent route) | 33.32 | 2.06 | 0.167 | 0.039 |

Optical micrographs comparing the control and the solution masterbatch samples were obtained but did not show visual improvement. However, the physical properties are more dramatically improved than in Example 1.

Based upon the foregoing disclosure, it should now be apparent that the present invention provides a process for the preparation of surface-stabilized, non-agglomerated silica. Also provided is a silica that has been surface stabilized before it could agglomerate. It is to be understood that any variations evident fall within the scope of the claimed invention and thus, the selection of specific process parameters can be determined without departing from the spirit of the invention herein disclosed and described. Thus, the scope of the invention shall include all modifications and variations that may fall within the scope of the attached claims.

What is claimed is:

1. A process for preparing surface-stabilized, non-agglomerated silica dispersed in a polymer comprising the steps of:
    providing colloidal silica;
    stabilizing the surface of the colloidal silica by esterification in the presence of a catalyst; and
    blending the surface-stabilized silica with a polymer solution, and optionally at least one additive, thereby substantially preventing agglomeration of the silica.

2. A process for preparing surface-stabilized, non-agglomerated silica dispersed in a polymer comprising the steps of:
    providing colloidal silica in a first solvent;
    performing a solvent exchange operation with an alcohol, whereby the first solvent is exchanged for the alcohol;
    adding at least one alcohol capable of esterifying the surface of the silica;
    esterifying the silica;
    distilling off water and the alcohols;
    dissolving the esterified silica in an organic solvent to form an organosol;
    blending the organosol with a polymer solution, and optionally at least one additive, to form a masterbatch; and
    desolventizing the masterbatch.

3. A process for preparing surface-stabilized, non-agglomerated silica in a rubber masterbatch comprising the steps of:
    providing colloidal silica in an aqueous first solvent;
    performing a solvent exchange operation with a second solvent selected from the group consisting of C4–C20 aliphatic, C5–C20 cycloaliphatic, C6–C20 aromatic, and C6–C20 alkyl aromatic solvents, whereby the first solvent is exchanged for the second solvent;
    reacting the silica in the second solvent with at least one hydrophobating agent to produce a surface-stabilized silica;
    blending the silica with a polymer solution, and optionally at least one additive, to form a masterbatch; and
    desolventizing the masterbatch.

4. The process of claim 3, wherein the step of reacting the silica further includes adding a catalyst.

5. A process for preparing surface-stabilized, non-agglomerated silica dispersed in a polymer comprising the steps of:
    providing colloidal silica in a first solvent;
    performing a solvent exchange operation with a second solvent, whereby the first solvent is exchanged for the second solvent;
    reacting the colloidal silica in the second solvent with a functionalized polymer to form a silica bound polymer; and
    desolventizing the silica bound polymer.

6. The process of claim 5, wherein the step of reacting the colloidal silica further includes adding a catalyst.

7. The process of claim 5, wherein the process further comprises blending the silica bound polymer with at least one additive prior to the desolventizing step.

8. A vulcanizable elastomeric composition of matter comprising surface-stabilized, non-agglomerated silica dispersed in a polymer, the silica produced by the process of claim 1.

9. A process for preparing surface-stabilized, non-agglomerated silica dispersed in a polymer comprising the steps of:
    reacting a silicate of at least one of an alkali metal and an alkaline earth metal in a first solvent with an acid and at least one hydrophobating agent to form a reaction product;
    performing a solvent exchange operation with a second solvent, whereby the first solvent is exchanged for the second solvent;
    blending the reaction product in the second solvent with a polymer solution, and optionally at least one additive, to form a masterbatch, and;
    desolventizing the masterbatch.

10. A vehicle tire, comprising:
    rubber comprising a surface-stabilized, non-agglomerated silica dispersed in a polymer.

11. The tire of claim 10, wherein the rubber is tread rubber.

12. An ink or toner, comprising:
    a colorant, a liquid, and surface-stabilized, non-agglomerated silica.

13. An orally inserted compound, comprising:
    a compound selected from the group consisting of a food, pharmaceutical, a dentifrice, and combinations thereof; and
    a surface-stabilized, non-agglomerated silica.

14. The process of claim 3 wherein the second solvent comprises isomers of hexane, either individually or in combination.

15. A surface-stabilized, non-agglomerated silica dispersed in a polymer, the silica produced by the process of claim 3.

16. A reinforcing filler for elastomeric compositions comprising surface-stabilized silica dispersed in a polymer, the silica produced by the process of claim 3.

17. A vulcanizable elastomeric composition of matter comprising surface-stabilized, non-agglomerated silica dispersed in a polymer, the silica produced by the process of claim 3.

* * * * *